United States Patent [19]

Starr et al.

[11] Patent Number: 5,570,689
[45] Date of Patent: Nov. 5, 1996

[54] RESPIRATORY MASK HAVING A VERTICALLY ADJUSTABLE SPACER ELEMENT THAT LIMITS SEAL DEFORMATION ON A WEARER'S FACE

[75] Inventors: Eric W. Starr; John R. Pujol; Andrew Serowski, all of Pittsburgh, Pa.

[73] Assignee: Respironics, Inc., Murrysville, Pa.

[21] Appl. No.: 431,626

[22] Filed: May 1, 1995

Related U.S. Application Data

[63] Continuation of Ser. No. 129,440, Sep. 30, 1993, abandoned.

[51] Int. Cl.⁶ .................................................. A62B 18/08
[52] U.S. Cl. ......................... 128/207.11; 128/206.27; 128/206.24
[58] Field of Search ........................ 128/206.23, 206.24, 128/206.25, 206.26, 206.27, 207.11, 206.15, 206.17, 206.21, 205.25

[56] References Cited

U.S. PATENT DOCUMENTS

| | | | |
|---|---|---|---|
| 1,000,706 | 8/1911 | Barnum | 128/207.11 |
| 1,105,127 | 7/1914 | Drager | 128/206.26 |
| 1,630,209 | 5/1927 | Olgard | 128/206.26 |
| 2,005,072 | 6/1935 | Bookarin | 128/206.26 |
| 2,106,795 | 2/1938 | Cover | 128/206.24 |
| 2,199,231 | 4/1940 | Schwartz | 128/206.17 |
| 2,540,567 | 2/1951 | Bennett | 128/206.26 |
| 2,910,063 | 10/1959 | Monroe et al. | 128/207.11 |
| 3,343,535 | 9/1967 | Lytle et al. | 128/206.24 |
| 4,907,584 | 3/1990 | McGinnis | 128/206.24 |
| 5,143,061 | 9/1992 | Kaimer | 128/206.24 |
| 5,191,882 | 3/1993 | Vogliano | 128/206.23 |
| 5,243,971 | 9/1993 | Sullivan et al. | 128/206.24 |
| 5,355,878 | 10/1994 | Griffiths et al. | 128/206.24 |

FOREIGN PATENT DOCUMENTS

| | | | |
|---|---|---|---|
| 529345 | 9/1921 | France | 128/206.24 |

Primary Examiner—Kimberly L. Asher
Attorney, Agent, or Firm—Reed Smith Shaw & McClay

[57] ABSTRACT

A respiratory mask including a flexible seal member that is formed to receive nasal and/or oral portions of a user's face. The flexible seal member is adapted to resiliently deform against the facial structure of the user to form a seal therewith when the mask is secured to the user's head by suitable straps or related headgear. The mask further includes a single block-like spacer for limiting deformation of the mask seal when the mask is engaged with the user's face and an adjustment mechanism for adjusting the position of the spacer. A presently preferred adjusting mechanism includes a flexible strap member upwardly extending from the mask and along which the spacer may be conveniently and selectively positioned.

5 Claims, 1 Drawing Sheet

RESPIRATORY MASK HAVING A VERTICALLY ADJUSTABLE SPACER ELEMENT THAT LIMITS SEAL DEFORMATION ON A WEARER'S FACE

This is a continuation of application(s) Ser. No. 08/129,440 filed on Sep. 30, 1993, now abandoned.

FIELD OF THE INVENTION

The present invention relates in general to respiratory masks and, in particular, to a respiratory mask including structure for enhancing the quality and comfort of the mask seal against a user's face.

BACKGROUND OF THE INVENTION in the art of respiration devices, there are a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

A requisite of such respiratory masks is that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

A significant class of such respiratory masks are those which incorporate a flap seal of thin material so positioned about the periphery of the mask as to provide self-sealing action against the face of the user when positive pressure is applied within the mask. With this type of sealing action, the forces exerted by retention or straps which serve o hold the mask in confronting engagement on the face f the user are typically and intentionally quite small. If the flap seal is capable of conforming to he contours of the user's face without forming leak paths, the mask can be used with retention straps which exert little or no net force to push the mask against the user's face. Thus, the overall sensation of constrain m and confinement is dramatically reduced for the user. Such a mask, when properly adjusted, can be adapted to any positive internal mask pressure. The sealing flap will be self-sealing as long as there is no looseness in the strapping arrangement which would allow the mask to move away from the face further than the reach of the sealing flap when subjected to internal pressure.

Flap seal-type masks are subject to certain potential limitations, however. By design, the flap of such masks seals by laying flat against the user's face throughout its length. This action requires a close match between the contours of the face and those of the seal. If the match is not good, the seal will be ineffective. Further, the normal response of one applying the mask to one's face is to push the mask harder against the face if the mask does not seal. With the typical flap seal-type mask, increasing contact pressure against the face will not help to form an effective seal if the flap seal does not initially fit well to the facial contours. It may, however, lead to patient discomfort and other problems.

A number of the above-described disadvantages of flap seal-type masks were addressed and effectively overcome by the respiratory mask and accessories described in U.S. Pat. No. 4,907,584. Of the many beneficial features of the mask described therein, two in particular operate to eliminate the mask seal problems naturally attendant to such masks. First, the flap seal's supportive sidewalls include a plurality of reinforcement ribs to prevent collapse or buckling of the mask seal. Second, the mask includes spacer means for limiting deformation of the seal when in engagement with the user's face. The combined effects of these features result in a mask capable of reliable and comfortable sealing with a user's facial contours. In the featured embodiment, the spacer means consists of a spacer block attached to a pressure sensitive adhesive strip which can be adhesively applied to the mask. Due to the fact that each user's facial contours are different, that document acknowledges that a family of several differently configured spacer blocks should be made available to the consumer/mask-user to adequately accommodate the varied mask sealing requirements of the user population. As possible alternatives to a family of spacer blocks, that reference also suggests mechanically adjustable screw spacer apparatus or inflatable balloon-like spacers (neither of which systems is accompanied by illustration).

While the spacer means notion, per se, is meritorious, the various spacer means disclosed in U.S. Pat. No. 4,907,584 are somewhat undesirable in terms of cost and practicality. That is to say, a respiratory mask "package" including a family of spacer blocks necessarily results in a more expensive system than one requiring but a single spacer. Moreover, the construction of the spacer blocks is such that a user may have to perform substantial and potentially time-consuming trial-and-error experimentation in respect to proper selection of spacer size and placement before the appropriate sealing effect is achieved. Indeed, the user cannot adjust the position of the spacer block relative to the mask (and, ultimately, the user's face) unless the user completely removes the block and its adhesive base from the mask and positions the block at another site on the mask. Moreover, the mask must be removed from the user's face each time the position of a spacer block is adjusted or a different spacer block is applied. As to the un-illustrated adjustable screw spacer mechanism and the inflatable balloon-like spacer, it will be readily appreciated that such constructions would likely be substantially more complex and, therefore, costly than a family of interchangeable blocks.

An advantage thus exists for a respiratory mask including a single block-like spacer means for limiting deformation of the mask seal when in engagement with a user's face, and means carried by the mask for enabling quick, easy and continuous adjustment of the vertical position of the spacer means to achieve optimum user comfort and sealing effect.

SUMMARY OF THE INVENTION

According to the present invention, there is provided a respiratory mask including a flexible seal member that is formed to receive nasal and/or oral portions of a user's face. The flexible seal member is adapted to resiliently deform against the facial structure of the user to form a seal therewith when the mask is secured to the user's head by suitable straps or related headgear. The mask further includes a single block-like spacer means for limiting deformation of the mask seal when the mask is engaged with the user's face, as well as means for adjusting the position of the spacer means. A presently preferred spacer adjusting means includes a flexible strap member upwardly extending from the mask and along which the spacer means may be conveniently and selectively positioned. By virtue of this arrangement, an uncomplicated, inexpensive and easily operated spacer adjustment system is provided whereby a high-quality, comfortable seal is created between the mask and the user's face.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
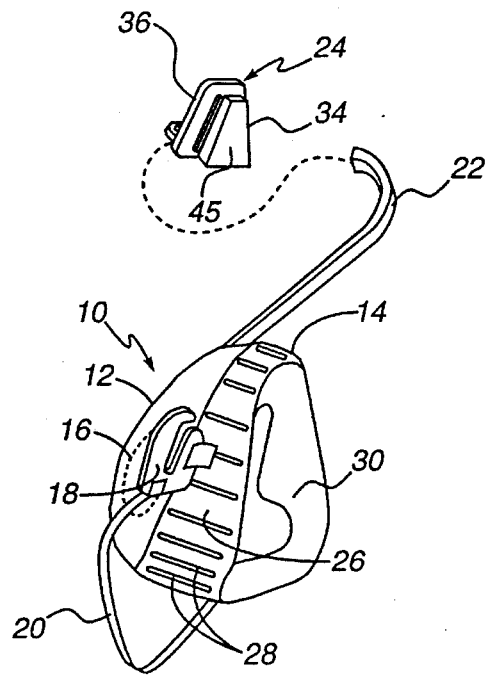
FIG. 1 is an exploded isometric view of the respiratory mask and spacer means of the present invention.

There is generally indicated by reference numeral 10 a respiratory mask constructed according to a presently preferred embodiment of the instant invention. Mask 10 includes a shell or body portion 12 which is preferably a generally rigid structural shell to which is joined a flexible, resilient, unitary seal member 14 of a type similar to that shown in U.S. Pat. No. 4,907,584.

Figure 3:
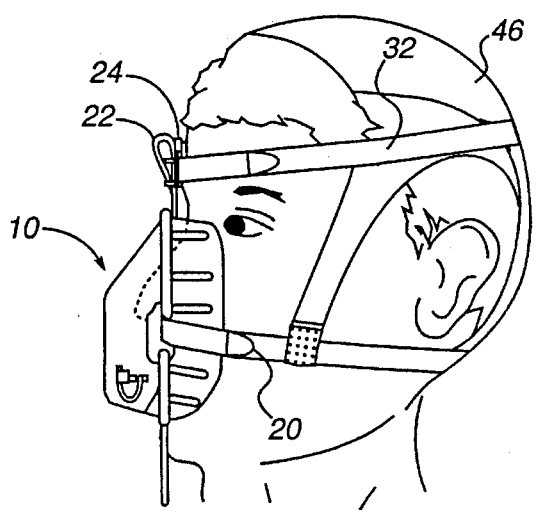
FIG. 3 is a side view of a user wearing the respiratory mask and spacer means of the present invention.

Shell portion 12 defines in a forepart thereof an opening 16 (shown in phantom line) or other suitable means for connecting mask 10 to a supply of gas. The mask as shown is an oral/nasal mask, i.e., it is sufficient in size to cover the nose and mouth of the user; see FIG. 3. It will be understood, however, that mask 10 may also be an exclusively oral or exclusively nasal mask whereby it respectively covers just the patient's mouth or nose. Shell portion 12 further includes two oppositely directed, laterally projecting strap retaining tabs 18 (only one of which is shown in FIGS. 1 and 3), from which depend conventional retention strap means 20 (hereafter referred to as the "lower strap means") for retaining the mask against the face of the user during use of the mask. Upwardly extending from the mask 10 is adjustment means 22 for adjusting the position of spacer means 24, both of which will be described in greater detail hereinafter.

Seal member 14 includes a peripheral all portion 26 which is desirably structurally reinforced by suitable means such as a plurality of ribs 28, or the like, whereby the seal member is prevented from collapse during operation. Integrally formed with wall portion 26 and projecting radially inwardly thereof is a seal flap 30 which defines an opening to receive the user's mouth and/or nose and forms a contoured sealing surface for confronting sealing engagement with the user's face. Oftentimes, the contours of the user's face are such that a comfortable and adequate seal may be achieved between face and mask merely by appropriate tightening of lower strap means 20. For many users, however, a second set of strap means 32 (hereinafter referred to as the "upper strap means" and shown in FIG. 3) must be utilized to attain the desired degree of comfort and sealing effect. It is at such times that the aforementioned spacer means 24 is brought into cooperating relationship with the adjustment means 22 to establish a spacer adjustment system capable of producing a high-quality, comfortable seal between the respiratory mask and the user's face essentially regardless of the user's facial contours.

Figure 2:
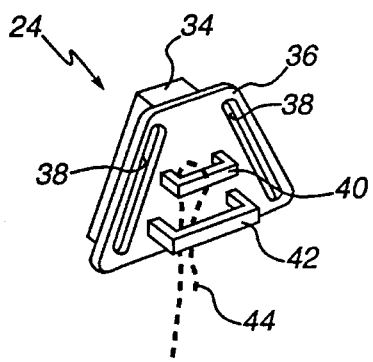
FIG. 2 is an enlarged isometric view of a side of the spacer means opposite to that shown in FIG. 1.

As is perhaps most clearly depicted in FIG. 2, the spacer means of the instant invention is for use in defining a predeterminable, minimum standoff distance between selected portions of the mask structure, for example the shell portion and seal member interface, and the user's face, to thereby enforce a predeterminable, limited deformation of the seal member 14 which may be imposed upon application of the mask to the user's face. The spacer means 24 preferably comprises an assembly including a block-like spacer element 34 affixed to a backing such as a generally rigid plate 36 formed of plastic or other suitable material and provided with elongated apertures 38 through which the upper strap means are adapted to be received in the manner indicated in FIG. 3. The plate 36 also includes means for cooperatively engaging with adjustment means 22. The presently preferred construction of the cooperatively engaging means includes a pair of upper and lower U-shaped openings 40 and 42 which are adapted to receive the adjustment means 22. In this connection, adjustment means 22 desirably assumes the form of an elongated flexible ribbon or strap which may be fixedly or detachably connected (such as by a clip, snap, Velcro® or the like) to mask 10. As shown by the dotted line 44 in FIG. 2, the free end of the adjustment means 22 will, under normal conditions, be threaded upwardly through the somewhat larger lower opening 42, then be looped around the upper opening 40 and pass downwardly through the lower opening 42. So threaded, the spacer means 24 is connected to the respiratory mask 10 in a manner whereby the position of the spacer means may be quickly, easily and continuously adjusted vertically relative to the mask through a range limited only by the length of adjustment means 22. It will be appreciated that the coefficients of friction and relative dimensions of the adjustment means and openings 40 and 42 are such that the spacer means securely maintains the desired vertical position selected by the user.

It is contemplated that other suitable means may be employed to enable continuous vertical adjustment of spacer means 24. For example, U-shaped openings 40, 42 may be separated by a small ridge extending generally parallel thereto. With such a construction, the flexible strap adjustment means 22 may be threaded upwardly through the lower loop 42, then directed to pass up one side and then down the other side of the ridge whereupon it may be threaded through the upper loop 40. In this fashion, the spacer means may be simply slid up or down along the adjustment strap 22 with friction again acting to retain the spacer means at the selected position. A further embodiment would have a rivet in lieu of the upper and lower loops 40 and 42, which rivet would project through and frictionally cooperate with a slit provided along the length of adjusting strap 22. According to another contemplated embodiment, the adjusting strap may be provided with a series of raised formations along its length projecting a distance from the strap surface sufficient to interferingly yet releasably engage loops 40 and 42 so as to permit incremental adjustment of the spacer means relative to the strap. These represent but a sample of the possible variations of adjustment mechanisms which may satisfy the objects of the present invention. Accordingly, then, they should be viewed as illustrative, but not limitative, of those adjustment mechanisms which might find utility in the instant invention.

The spacer element 34 may be of any suitable material consistent with the objectives of light weight, economy, and user comfort. For example, a spacer element of foam rubber may be suitable, given that the foam rubber material is of sufficient resilience and stiffness to define a distinct standoff distance between the mask and the user's face without presenting any surfaces so hard that they would produce discomfort when in contact with the user's face. From this, it will be appreciated that the spacer element may also be of laminated or laid-up construction, or a variety of other known structures consistent with the stated objectives.

In use as described, and as shown in FIG. 3, the spacer means 24 is engaged with the adjustment means 22 such that a facial contact surface 45 thereof (FIG. 1) is oriented a direction facing the user. The mask is then applied to the user's face with the spacer means 24 defining the limit of deformation for seal member 14 adjacent the upper portions thereof. The upper and lower strap means 32 and 20 which may form part of a suitable head harness arrangement 46, as shown, are then respectively connected with the Spacer means apertures 38 and the strap retaining tabs 18. Thereafter, the spacer means 24 is adjusted to an appropriate vertical position for comfort and good sealing effect and the strap means are tightened just sufficiently to deform the seal member 14, with the upper portion thereof at the prescribed standoff distance, into sealing engagement with the user's face. If, however, the spacer means 24 is not in an optimum position upon tightening of the strap means, the spacer means may be slid upwardly or downwardly along the adjustment strap means 24 until such position is found, without removing the mask.

Although the invention has been described in detail for the purpose of illustration, it is to be understood that such detail is solely for that purpose and that variations can be made therein by those skilled in the art without departing from the spirit and scope of the invention except as it may be limited by the claims.

We claim:

1. In a respiration system adapted for administering breathing gas to a user, the combination comprising:

a mask body having an adjustment strap attached to and extending substantially vertically from an upper portion of said mask body;

a flexible sealing member joined to said mask body and adapted to be placed in confronting contact with a portion of the face of user to form a seal therewith; and means for limiting deformation of said sealing member when said sealing member is in contact with a user's face, said means for limiting deformation including means for an element cooperating with said adjustment strap and connected for vertical adjustment along said adjustment strap, said means for limiting deformation of sealing member with respect to a user's face not requiring disengagement of said means for limiting deformation and said adjustment strap.

2. The combination of claim 1 wherein said element cooperating with said adjustment strap comprises a plurality of openings through which said adjustment strap is adapted to threadably extend.

3. The combination of claim 1 wherein said means for limiting deformation includes an assembly comprising said element affixed to a backing and said element is a spacer element.

4. The combination of claim 3 wherein said backing includes means for connecting said assembly to retention straps adapted for retaining said spacer element against a user's face.

5. The combination of claim 3 wherein said spacer element is formed of resilient material.

\* \* \* \* \*

UNITED STATES PATENT AND TRADEMARK OFFICE
CERTIFICATE OF CORRECTION

PATENT NO. : 5,570,689
DATED : November 5, 1996
INVENTOR(S) : STARR et al.

It is certified that error appears in the above-indentified patent and that said Letters Patent is hereby corrected as shown below:

Column 6, line 16 (i.e. line 12 of Claim 1), delete "means".

Column 6, line 19 (i.e. line 15 of Claim 1), insert --said-- between "of" and "sealing".

Signed and Sealed this

Fourteenth Day of July, 1998

*Attest:*

BRUCE LEHMAN

*Attesting Officer*  *Commissioner of Patents and Trademarks*